Figure 1:
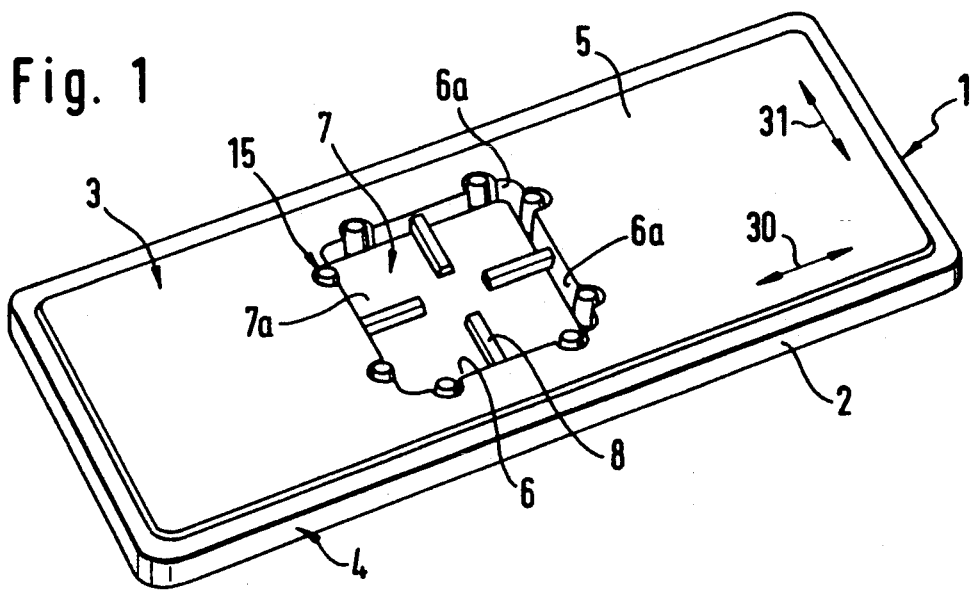

United States Patent [19]

Krause et al.

[11] Patent Number: 5,173,261
[45] Date of Patent: Dec. 22, 1992

[54] TEST CARRIER FOR THE ANALYSIS OF FLUIDS

[75] Inventors: Manfred Krause, Viernheim; Gerhard Schindler, Grünstadt, both of Fed. Rep. of Germany

[73] Assignee: Boehringer Mannheim GmbH, Mannheim, Fed. Rep. of Germany

[21] Appl. No.: 778,096
[22] PCT Filed: Apr. 12, 1991
[86] PCT No.: PCT/DE91/00310
 § 371 Date: Dec. 12, 1991
 § 102(e) Date: Dec. 12, 1991
[87] PCT Pub. No.: WO91/16626
 PCT Pub. Date: Oct. 31, 1991

[30] Foreign Application Priority Data

Apr. 14, 1990 [DE] Fed. Rep. of Germany ....... 4012216

[51] Int. Cl.$^5$ ............................................. G01N 33/52
[52] U.S. Cl. ..................................... 422/58; 435/970;
435/805; 422/56; 422/68.1; 436/170; 436/524
[58] Field of Search ..................... 422/55, 56, 57, 58,
422/68.1; 435/805, 970; 436/66, 524, 169, 170

[56] References Cited

U.S. PATENT DOCUMENTS

| | | |
|---|---|---|
| 4,181,500 | 1/1980 | Cowsar et al. ........................ 422/58 |
| 4,254,083 | 3/1981 | Dolumbus ............................ 422/56 |
| 5,006,464 | 4/1991 | Chu et al. ............................. 422/58 |
| 5,071,746 | 12/1991 | Wilk et al. ........................... 422/68.1 |
| 5,073,340 | 12/1991 | Covington et al. ................... 422/57 |
| 5,104,619 | 4/1992 | De Castro et al. ................... 422/57 |
| 5,106,758 | 4/1992 | Adler et al. .......................... 422/58 |

FOREIGN PATENT DOCUMENTS

| | | |
|---|---|---|
| 0186100 | 12/1985 | European Pat. Off. . |
| 0198628 | 4/1986 | European Pat. Off. . |
| 0269876 | 10/1987 | European Pat. Off. . |
| 0334015 | 2/1989 | European Pat. Off. . |
| 0352690 | 7/1989 | France . |
| 0066648 | 12/1982 | Japan . |

Primary Examiner—James C. Housel
Assistant Examiner—Ramon Torres
Attorney, Agent, or Firm—Nikaido, Marmelstein, Murray & Oram

[57] ABSTRACT

Test carrier for the analysis of fluids with a test field (7) held in a frame (2), in which the frame (2) comprises a top part (3) and a base part (4) and at least the top part (3) comprises a test field opening (6) through which a sample fluid can be applied to the surface (7a) of the test field. Simplified handling and improved analytical reliability are achieved by the fact that the base part (4) comprises a seat (16) for the test field (7) which is surrounded by positioning elements (15) which are higher than the test field (7). The test field opening (6) is greater than the test field (7), so that the rim (18) of the test field is visible. The top part (3) comprises pressure tongues resting on the surface (7a) of the test field (7) and projecting into the test field opening (7).

9 Claims, 2 Drawing Sheets

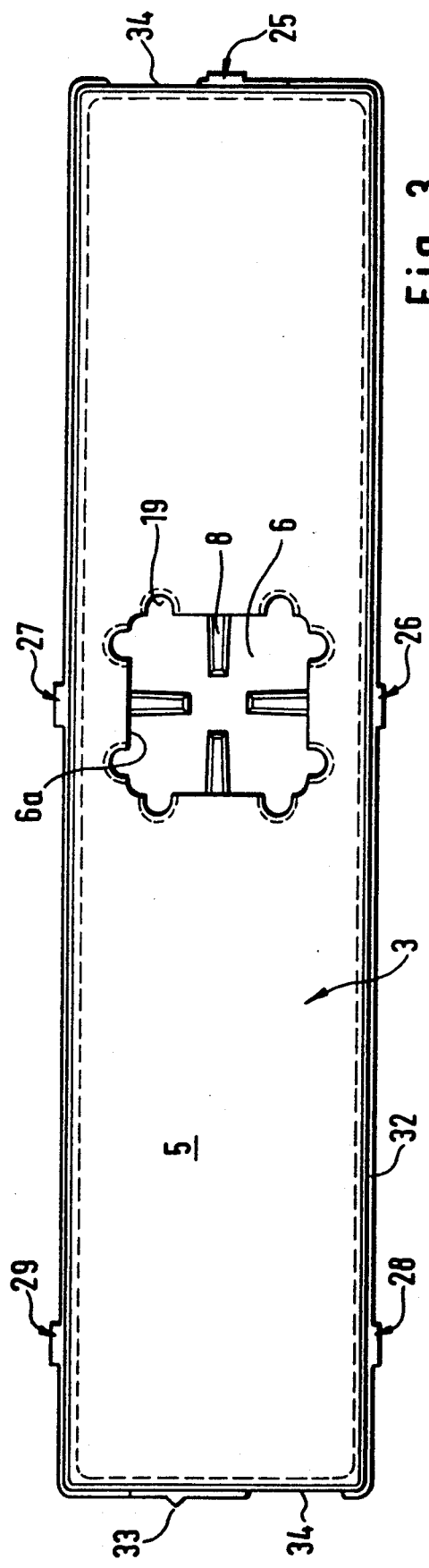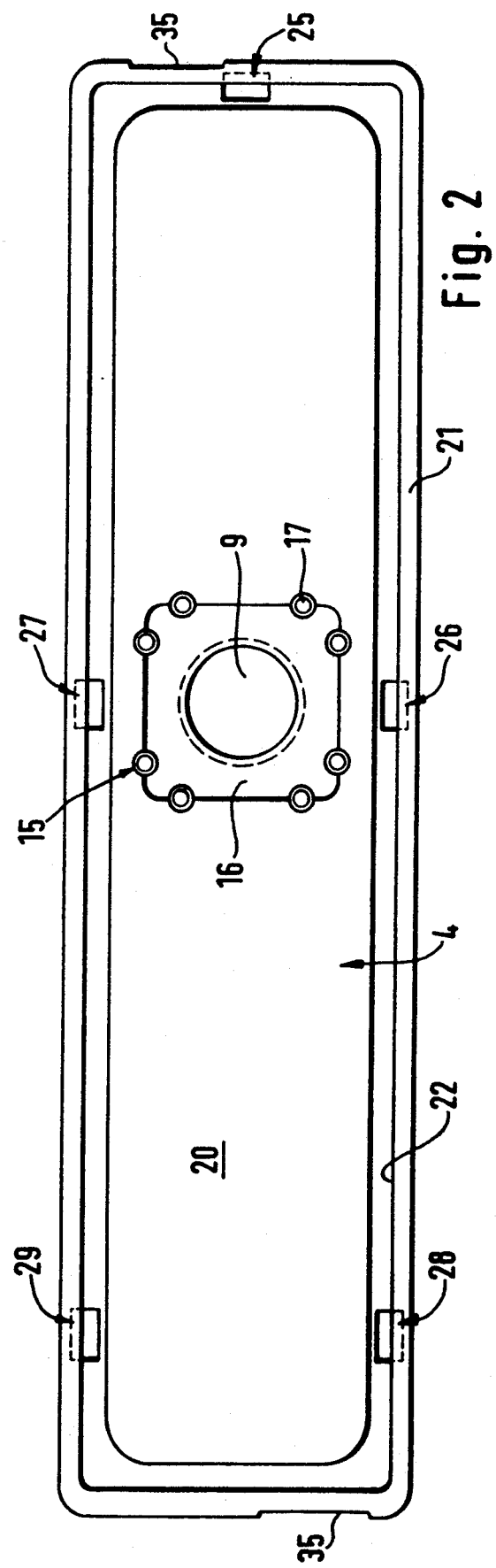

TEST CARRIER FOR THE ANALYSIS OF FLUIDS

The invention relates to a test carrier for the analysis of fluids with a test field held in a frame, in which the frame comprises a top part and a base part and at least the top part comprises a test field opening through which a fluid sample can be applied to the surface of the test field.

For the qualitative or quantitative analytical determination of constituents of fluids, in particular body fluids of humans or animals, so-called carrier-bound test are increasingly being used. In the latter, reagents are embedded in the test layers of an analysis element designated overall as a test carrier. They are brought into contact with the sample. The reaction of sample and reagents leads to a detectable signal, in particular a colour change, which can be evaluated visually or by means of an apparatus, in most cases reflection-photometrically. Many different types of test carrier are known, which differ from one another not only with respect to the reagents used, but also in their construction, in particular as regards the arrangement and fixing of the test layers. The following type is of particular practical importance.

Strip-type test carriers consist mainly of an elongated carrying layer of plastics material and test layers attached thereto. The connection between the test layers and the plastics carrier is usually made by bonding, and the bonding in many cases does not take place over the whole surface, but only on one edge of the test layer, or additional fixing means (nets or fixing foils) are fixed to the carrying layer, which secure the test layers indirectly. In this way a very varied arrangement of the test layers next to one another and/or on one another, according to the requirements of the individual test, is possible. The test layers can be manufactured independently of one another and be joined together during the final assembly of the strip-type test carrier.

The invention is directed towards the type of test carrier mentioned at the outset, in which a test field is held by a frame similarly to a photographic slide. They are referred to below as "test carriers with frames" and in the English-language literature as "analysis slides". The sample is in this case usually applied through the test field opening onto one side (top side) of the test field. On the conclusion of the test reaction the colour formation can be observed or measured, usually on the side of the test field facing away from the sample side (bottom side of the test field).

The aim of the invention is to provide a test carrier with frame which is distinguished by simplified handling and improved analytical reliability.

The aim is achieved in the case of a test carrier of the kind described at the outset by the fact that the base part comprises a seat for the test field, the seat in the base part is surrounded by positioning means for the test field, the test field opening is greater than the test field, so that the rim of the test field is visible, and the top part comprises pressure tongues resting on the top surface the test field and projecting into the test field opening.

In the case of the previously known test carriers with frame the test field opening through which the blood sample is applied (blood application opening) was always smaller than the test field. The top part of the frame rested with a peripheral pressure face against the rim of the test field. Said arrangement was regarded as necessary in order to achieve adequate positioning and flatness of the test field. In addition it was assumed that only with a test field opening which covered the rim of the test field lateral flowing by of the blood could be prevented.

Here the invention demonstrates a radically different method, which proves to be exceptionally advantageous.

The top side of the test field can be seen in almost its entirety. In this way it becomes possible to inspect visually whether a sufficient amount of fluid sample has been applied and whether the test field is completely wetted. During the analysis of blood, in particular, incomplete wetting may be recognized easily by the fact that parts of the fluid-absorbing test field are not coloured or not coloured uniformly. The handling of the test carrier is simplified, because it is easier to apply the blood sample to the test field in an accurately aimed manner.

In addition the invention makes it possible to use test fields with a very small surface area (less than 50 $mm^2$, preferably less than 30 $mm^2$). Said arrangement is of particular importance if, according to a preferred embodiment, the test field is constructed as a test layer package consisting of a plurality of loosely superimposed test layers. Said arrangement is advantageous in many cases, because in this way test layers with very different structures may be combined with one another. Thus, for example, fibre composite structures (woven or non-woven fabric), fine-pored plastics layers ("membranes") and bonded particle structures (e.g. EP-A-0 013 156) each have specific properties which are advantageous for particular applications. A test layer package consisting of a plurality of loosely superimposed layers usually has, however, a fairly high fluid requirement per unit of area so that the possibility of working with a very small surface area is particularly advantageous. It has also, surprisingly, proved to be sufficient if the layers of the test layer package are held only by the relatively long and narrow pressure tongues.

Figure 5:
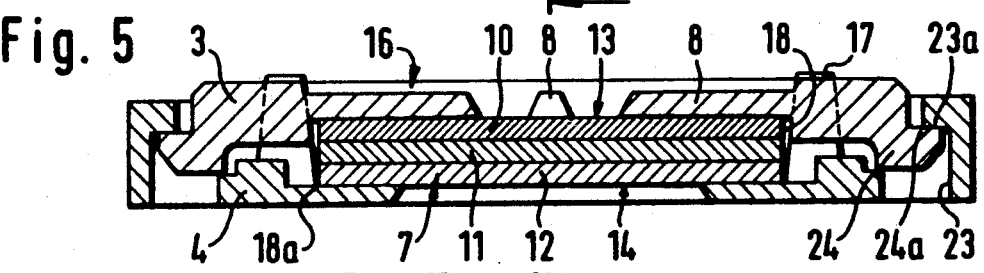
Figure 6:
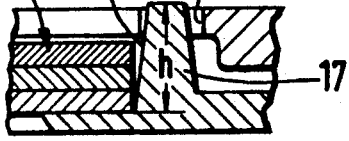

The invention will be explained in detail below with reference to an exemplifying embodiment shown in the figures, where FIG. 1 shows a perspective view of a test carrier according to the invention, FIG. 2 a top view of a base part, FIG. 3 a top view of a top part, FIG. 4 an enlarged top view of a test carrier according to the invention, FIG. 5 an enlarged cross-section through a test carrier according to the invention along the line V—V in FIG. 4, FIG. 6 a partial cross-section along the line VI—VI in FIG. 4.

The test carrier 1 shown in FIG. 1 has a flat, preferably less than 3 mm, particularly preferably only about 2 mm, thick frame 2 which consists of a top part 3 and a base part 4. In the centre of the upper frame surface 5 there is located a first test field opening 6 (sample application opening), through which the top side 7a of the test field 7 is visible. Pressure tongues 8 lie flat on the test field 7, which start from the edge 6a of the test field opening 6.

DETAILS ARE SHOWN IN FIGS. 2 TO 5.

The test field 7 is in the preferred case shown constructed as a test layer package consisting of three loosely superimposed test layers 10, 11, 12. It could however also consist of a single layer or of a layered composite in which the layers are manufactured on top of one another by liquid coating and are thus joined over their whole area. The layers fulfil different functions in the test process. For example the topmost test layer 10 may be a covering mesh which protects the layers beneath it and at the same time contains a wetting agent which promotes the spreading of the sample. The layer 11 may serve to separate the erythrocytes out of the blood sample. A glass fibre mat according to U.S. Pat. No. 4 477 575 is suitable for example. The layer 12 may for example be a reagent film containing a reagent system which leads to a colour change characteristic for the analysis on the underside of the layer 12. Details of the test sequence are not important for the present invention. As a rule, however, the test sequence is such that the sample is fed on one side of the test layer package, which can be designated as the sample feed side 13, and the measurement or visual evaluation of the detection signal takes place on the other side of the test layer package (detection side 14) through a second test field opening 9 (measurement opening).

In the base part 4 a seat 16 is provided for the test field 7. The test field 7 is surrounded in the seat by positioning means 15 which are higher than the test field, in the preferred case shown therefore higher than the test layer package 10, 11, 12.

The positioning means may be formed by a continuous wall limiting the seat 16 and surrounding the test field 7. Discrete, pillar-shaped limiting elements 17 are however preferably used. The pillar-shaped limiting elements 17 may exhibit various cross-sections, for example trigonal or polygonal. In the case shown the limiting elements 17 have a circular cross-section. In general it has proved to be advantageous if the contact surfaces on which the limiting elements are in contact with the rim 18 of the test field 7 are as small as possible. A shape of the limiting elements which ensures line contact with the rim 18 of the test field 7 is preferred. This is the case for example with the circular cross-sectional shape shown. Alternatively, however, a polygonal shape could also be chosen, in which a corner or a narrow land butts against the rim 18 of the test field 7.

By the use of discrete limiting elements 17, on the one hand an exact positioning is achieved. On the other, no extensive capillary gaps are present through which sample fluid could be sucked off in an undesirable manner. A cavity running round the rim of the test field remains unencumbered and may accommodate a surplus of sample fluid. The whole of the contact surface on which the limiting elements 17 make contact with the test field 7 at the rim 18 should for this reason make up preferably less than 25%, particularly preferably less than 10%, of the overall length of the test field rim 18.

According to a further preferred embodiment the limiting elements 17 are constructed so that their side 17a facing the test field 7 runs obliquely away from the test field from bottom to top. The spacings of the limiting elements 17 and the dimensions of the test field 7 are in addition coordinated with one another so that the bottom edge 18a of the rim 18 of the test field 7 is bordered by the limiting elements 17 with very little clearance. In this way the exact positioning required for a precise analysis is achieved and at the same time simple and rational mechanical assembly is made possible. This applies in particular to the case of a test layer package 10, 11, 12 in which the lowest test layer 12 is positioned very precisely, while the test layers 11 and 10 lying above it are introduced into the seat 16 with a certain clearance.

The top part 3 comprises recesses 19 into which the limiting elements 17 penetrate. The limiting elements 17 thus have a sufficient height h required for the rational assembly of the test carrier 1 (at least 20% more than the overall thickness of the test layer package 10, 11, 12) which may with advantage be combined with an exceptionally flat construction of the frame 2.

Figure 4:
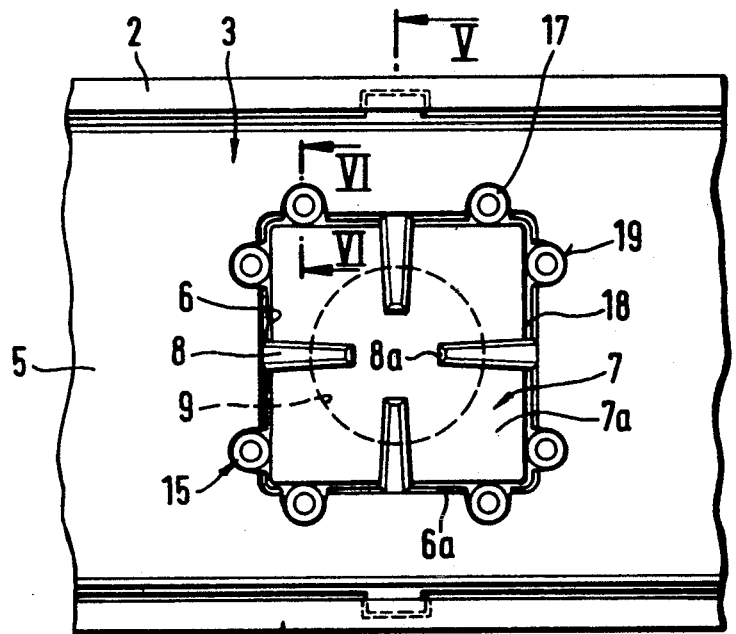

In FIG. 4 it can be seen particularly clearly that the test field 7 is smaller than the sample application opening 6, so that the rim 18 of the test field 7 is, apart from the cross-section of the pressure tongues 8, visible over its entire length. The recesses 19 are formed by bulges in the edge 6a of the test field or blood application opening 6.

The pressure tongues 8 project relatively far in the direction of the middle of the test field 7 into the opening 6. Their length should be at least approx. 20%, preferably at least 30%, of that dimension of the test field opening 6 in which the respective tongue 8 extends. Its end 8a projecting into the test field opening 6 lies above the lower test field opening 9 shown in dashes in FIG. 4, through which the measurement takes place.

The connection of the top part 3 to the base part 4 is preferably undertaken by adhesive-free discrete connection elements 25, 26, 27, 28, 29 which are preferably constructed so that they comprise respectively limiting elements 23a, 24a (FIG. 5) which butt positively against one another and limit the relative movement perpendicular to the plane of the test layer package 7. In the case shown the top part 3 has a projection 24 whose upper surface forms one of the limiting elements. The base part 4 has recesses 23 which are open towards the centre of the frame 2, and on which the limiting elements 23a on the base part side are formed. The projections 24 engage with the recesses 23. One projection 24 and one recess 23 respectively form a connection element 25 to 29. Different configurations of the connection elements are possible, but it is advantageous if they are constructed so that on the one hand they limit in a defined manner the relative movement between top part and base part in the direction perpendicular to the test layers 10 to 12, while on the other they permit a slight relative movement of both parts in the direction parallel to the surface of the test layers 10 to 12, which facilitates the elastic deformation of top part 3 and base part 4.

The connection elements 25 to 29 are preferably constructed as clip connections, the positively interlocking parts 23, 24 being easily deformed elastically during assembly in order to force them into engagement with one another. The clip connection must be constructed so that it cannot work loose during the elastic deformation according to the invention.

In the exemplifying embodiment shown the base part 4 has, compared with its bottom surface 20, a thickened edge profile 21 against which the clip connections are formed.

In view of the desired elasticity of top part and base part it is advantageous if both are fixed only with comparatively few discrete adhesive-free connection elements with regard to a relative movement perpendicular to the plane of the test field and that the latter are spaced comparatively far apart.

In practice it is also important that top part and base part are positioned accurately relative to one another in the direction of their surface dimensions indicated by the arrows 30 and 31 in FIG. 1. For this purpose the top part has a narrow peripheral fitting strap 32 which rests against the inner wall 22 of the edge profile 21 of the base part 20. The exact location is obtained by means of a positioning lug 33.

The top part 3 and the base part 4 are preferably manufactured by the injection moulding of polystyrene or ABS (acrylonitrilebutadiene-styrene copolymer). They are with advantage provided at their edges with resilient recesses 34 and 35, against which the gate pins rest during the manufacturing process.

We claim:

1. Test carrier for the analysis of fluids with a test field held in a frame, in which the frame comprises a top part and a base part connected with the top part and at least the top part comprises a test field opening through which a sample fluid can be applied to an upper surface of the test field,
wherein
   the base part comprises a seat for the test field,
   the seat in the base part is surrounded by positioning means for the test field which are higher than the test field,
   the area of the test field opening is greater than the area of the upper surface of test field thereby forming a visible rim on the periphery of the upper surface of the test field, and
   the top part further comprises pressure tongues resting on the upper surface of the test field and projecting into the test field opening.

2. Test carrier according to claim 1, characterised in that the test field is constructed as a test layer package with at least two superimposed test layers not connected to one another over their whole area.

3. Test carrier according to claim 1, characterised in that the positioning means incorporate a plurality of discrete, pillar-shaped limiting elements.

4. Test carrier according to claim 3, characterised in that the limiting elements are so constructed that they stand in line contact with the rim of the test field.

5. Test carrier according to claim 3, characterised in that each limiting elements on a side thereof facing the test field runs obliquely away from the test field from bottom to top.

6. Test carrier according to claim 3, characterised in that the top part comprises recesses into which the pillar-shaped limiting elements penetrate.

7. Test carrier according to claim 1, characterised in that the top part and the base part are connected to one another by at least two connection elements which comprise respectively limiting elements butting positively against one another and limiting the relative movement of the parts perpendicular to the plane of the test layer package.

8. Test carrier according to a claim 7, characterised in that the connection elements are constructed as clip connections.

9. Test carrier according to claim 8, characterised in that one of the top part and the base part has an edge profile extending vertically about an outer periphery thereof and the clip connection engages with the edge profile.

* * * * *